United States Patent
Kato et al.

Patent Number: 6,156,175
Date of Patent: Dec. 5, 2000

[54] METHOD FOR PRODUCING ELECTROCHEMICAL ELEMENT AND ELECTROCHEMICAL ELEMENT

[75] Inventors: Nobuhide Kato, Ama-Gun; Kunihiko Nakagaki, Nagoya, both of Japan

[73] Assignee: NGK Insulators, Ltd., Nagoya, Japan

[21] Appl. No.: 09/191,734

[22] Filed: Nov. 13, 1998

[30] Foreign Application Priority Data

Nov. 17, 1997 [JP] Japan ................................ 9-315180

[51] Int. Cl.[7] ................................................ G01N 27/407
[52] U.S. Cl. .................... 204/424; 156/89.6; 204/425; 204/426; 204/427; 264/618; 264/620; 264/656; 264/676
[58] Field of Search ............................... 264/618, 619, 264/620, 656, 657, 676; 156/89.16; 204/421–429

[56] References Cited

U.S. PATENT DOCUMENTS

| | | | |
|---|---|---|---|
| 4,505,807 | 3/1985 | Yamada | 204/426 |
| 5,169,811 | 12/1992 | Cipollini et al. | |
| 5,252,519 | 10/1993 | Nakatani et al. | 437/209 |
| 5,419,857 | 5/1995 | Van den Sype | 264/656 |
| 5,736,095 | 4/1998 | Shimada et al. | 264/676 |

FOREIGN PATENT DOCUMENTS

| | | |
|---|---|---|
| 0 678 740 | 10/1995 | European Pat. Off. |
| 0 769 693 | 4/1997 | European Pat. Off. |
| 8-271476 | 10/1996 | Japan |

*Primary Examiner*—T. Tung
*Attorney, Agent, or Firm*—Burr & Brown

[57] ABSTRACT

A method for producing a NOx sensor comprises the steps of forming electrodes on ceramic green sheets, and stacking and integrating the ceramic green sheets into one unit followed by sintering to prepare a substrate, wherein an oxygen concentration is controlled to be not more than 0.5% in a sintering atmosphere after removal of a binder in the step of sintering the substrate. Specifically, the sintering is performed in an atmospheric atmosphere in Interval 1 in which the temperature in a furnace is changed from room temperature to about 1000° C., and the sintering is performed in a nitrogen atmosphere (oxygen concentration in the atmosphere in the furnace is controlled to be about 400 ppm) in Interval 2 in which the temperature is changed from 1000° C. to a maximum temperature followed by spontaneous radiational cooling. Accordingly, it is possible to suppress alloy formation on a detecting electrode for detecting a measurement gas component (for example, NOx), and it is possible to improve the measurement accuracy of the NOx sensor.

8 Claims, 9 Drawing Sheets

METHOD FOR PRODUCING ELECTROCHEMICAL ELEMENT AND ELECTROCHEMICAL ELEMENT

BACKGROUND OF THE INVENTION

1. Field of the Invention

The present invention relates to a method for producing an electrochemical element and the electrochemical element. In particular, the present invention relates to a method for producing an electrochemical element and the electrochemical element preferably used for a gas sensor for measuring oxide such as NO, $NO_2$, $SO_2$, $CO_2$, and $H_2O$, and inflammable gases such as $H_2CO$, and hydrocarbon (CnHm) contained in, for example, atmospheric air and exhaust gas discharged from vehicles or automobiles.

2. Description of the Related Art

Conventionally, those known as the method for measuring NOx in a measurement gas such as combustion gas include a technique in which the NOx-reducing ability of Rh is utilized while using a sensor comprising a Pt electrode and an Rh electrode formed on an oxygen ion-conductive solid electrolyte such as zirconia to measure an electromotive force generated between the both electrodes.

However, the sensor as described above suffers the following problem. That is, the electromotive force is greatly changed depending on the change in concentration of oxygen contained in the combustion gas as the measurement gas. Moreover, the change in electromotive force is small with respect to the change in concentration of NOx. For this reason, the conventional sensor tends to suffer influence of noise.

Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform correct measurement for a combustion gas produced under such a combustion condition.

In order to solve the problems as described above, for example, Japanese Laid-Open Patent Publication No. 8-271476 discloses a NOx sensor comprising pumping electrodes having different NOx-decomposing abilities arranged in a first internal space which communicates with a measurement gas-existing space and in a second internal space which communicates with the first internal space, and a method for measuring the NOx concentration in which the $O_2$ concentration is adjusted by using a first pumping cell arranged in the first internal space, and NO is decomposed by using a decomposing pumping cell arranged in the second internal space so that the NOx concentration is measured on the basis of a pumping current flowing through the decomposing pump.

Further, Japanese Laid-Open Patent Publication No. 9-113484 discloses a sensor element comprising an auxiliary pumping electrode arranged in a second internal space so that the oxygen concentration in the second internal space is controlled to be constant even when the oxygen concentration is suddenly changed.

In the case of the NOx sensor as described above, the decomposition of NOx theoretically begins at an element temperature of about 600° C. However, the decomposition of NOx actually begins at an element temperature of about 700° C. in the conventional gas sensor. Therefore, a problem arises in that the NOx-decomposing electrode such as an Rh electrode has poor operation performance at a low temperature.

It is considered that such a problem is caused as follows. That is, a part of the Rh electrode forms an alloy together with Pt and Au during the process of producing the NOx sensor, especially during the sintering process for the substrate. For this reason, the catalytic activity, which is originally possessed by Rh, is lowered. As a result, the NOx sensor has the poor operation performance at the low temperature.

In view of the consideration as described above, the present inventors observed a cross section of such a sensor element by using SEM (scanning electron microscope). As a result, it was found that an alloy was formed by Rh together with Pt and Au on the Rh electrode.

The mechanism for forming the alloy will now be explained. At first, Pt, which is a major material for the Pt electrode provided to be paired with the Rh electrode, is partially oxidized in atmospheric air in a region of not less than 1000° C. to form $PtO_2$. In general, $PtO_2$ has a high vapor pressure as compared with metallic Pt, and it has a volatile property.

Volatilized $PtO_2$ diffuses up to the Rh electrode provided in the substrate together with the Pt electrode, and it forms an alloy together with Rh. Especially, when Au, Ir, or various transition metals are added in order to suppress the catalytic activity of the Pt electrode, the volatilization of Pt is accelerated. As a result, the formation of the alloy of Rh, Pt, Au or the like is facilitated thereby. It is assumed that the acceleration of the volatilization of Pt is caused because the oxidation of Pt is accelerated by the addition of Au or the like to Pt.

When the alloy is formed, an extremely large amount of oxygen exists around the Rh electrode. In order to improve the measurement accuracy of the NOx sensor, it is necessary to eliminate the offset component upon the measurement as less as possible. Therefore, it is necessary that the oxygen existing around the Rh electrode should be once removed when the operation of the NOx sensor is started. As a result, a problem arises in that when the NOx sensor is used, it is necessary to wait for the start of actual measurement for a long period of time.

SUMMARY OF THE INVENTION

The present invention has been made taking the foregoing problems into consideration, an object of which is to provide a method for producing an electrochemical element and the electrochemical element which make it possible to suppress formation of any alloy, for example, on a detecting electrode for detecting a measurement gas component (for example, NOx) and improve the measurement accuracy of the electrochemical element.

The present invention lies in a method for producing an electrochemical element based on a limiting current system comprising electrodes composed of different materials or different compositions arranged in one internal space which is provided in a substrate of a solid electrolyte or in a plurality of internal spaces which communicate with each other, the method comprising the steps of forming the electrodes on ceramic green sheets, and stacking and integrating the ceramic green sheets into one unit followed by sintering to prepare the substrate, wherein an oxygen concentration is controlled to be not more than 0.5% in a sintering atmosphere after removal of a binder in the step of sintering the substrate.

In this description, an electrode (for example, a Pt electrode), which is formed of a material to be volatilized by oxidation, is referred to as "pumping electrode". An electrode (for example, an Rh electrode), which is used to decompose a measurement gas component and detect an amount of oxygen produced by the decomposition, is referred to as "detecting electrode".

According to the method described above, oxidation scarcely occurs on the pumping electrode. Accordingly, there is little diffusion of oxide to the detecting electrode. Thus, it is possible to suppress formation of any alloy on the detecting electrode.

If the oxygen concentration in the sintering atmosphere is suppressed to be low in a state in which the binder in the substrate remains, the binder remains as carbon. When the electrochemical element is used, for example, as a NOx sensor, the carbon causes a problem that combustion of the carbon takes place when the element temperature is raised, resulting in any error in the measurement output.

However, according to the present invention, the oxygen concentration in the sintering atmosphere is controlled after removing the binder. Therefore, the output error does not occur, which would be otherwise caused by the residual binder as described above. Thus, it is possible to reliably improve the measurement accuracy when the electrochemical element is used, for example, as a NOx sensor.

It is preferable in the method described above that the oxygen concentration in the sintering atmosphere is controlled to be not more than 500 ppm. In order to suppress the catalytic activity of the pumping electrode of the gas sensor, the pumping electrode is added with Au, Ir, or various transition metals. In such a situation, volatilization of the major component for constituting the pumping electrode is accelerated. However, when the oxygen concentration in the sintering atmosphere is controlled to be not more than 500 ppm, the acceleration of volatilization of the major component is suppressed. Thus, it is possible to effectively suppress the formation of the alloy on the detecting electrode.

It is also preferable in the method described above that the sintering step is started from an atmospheric atmosphere, and the control of the oxygen concentration is started from a predetermined temperature. In this embodiment, it is preferable that the control of the oxygen concentration is started at a temperature of not less than 400° C.

It is also preferable in the method described above that a state of controlling the oxygen concentration is restored again to an atmospheric atmosphere during a process of lowering temperature after completion of maintenance of a maximum temperature for a predetermined period of time during the sintering step. In this embodiment, it is preferable that introduction of the atmospheric atmosphere is started again at a temperature of not more than 1000° C.

It is also preferable in the method described above that $H_2O$ or $CO_2$ is added to an atmosphere in which the oxygen concentration is controlled in the sintering atmosphere.

In another aspect, the present invention lies in an electrochemical element comprising one internal space which is provided in a substrate of a solid electrolyte, or a plurality of internal spaces which communicate with each other, and two or more electrodes composed of different materials or different compositions arranged in the internal space or in the internal spaces, wherein at least the substrate is formed by sintering an integrated unit of stacked ceramic green sheets, in an atmosphere in which oxygen concentration is controlled to be not more than 0.5% in a predetermined temperature region.

According to the present invention, oxidation scarcely occurs on the pumping electrode. Accordingly, there is little diffusion of oxide to the detecting electrode. Thus, it is possible to suppress formation of any alloy on the detecting electrode.

Therefore, it is possible to reliably improve the measurement accuracy when the electrochemical element is used, for example, as a NOx sensor.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Explanation will be made below with reference to FIGS. 1 to 9 for an illustrative embodiment in which the method for producing the electrochemical element according to the present invention is applied, for example, to a process for producing a NOx sensor (hereinafter simply referred to as "production method according to the embodiment"), and for an illustrative embodiment in which the electrochemical element according to the present invention is applied, for example, to a NOx sensor (hereinafter simply referred to as "NOx sensor according to the embodiment").

Figure 1:
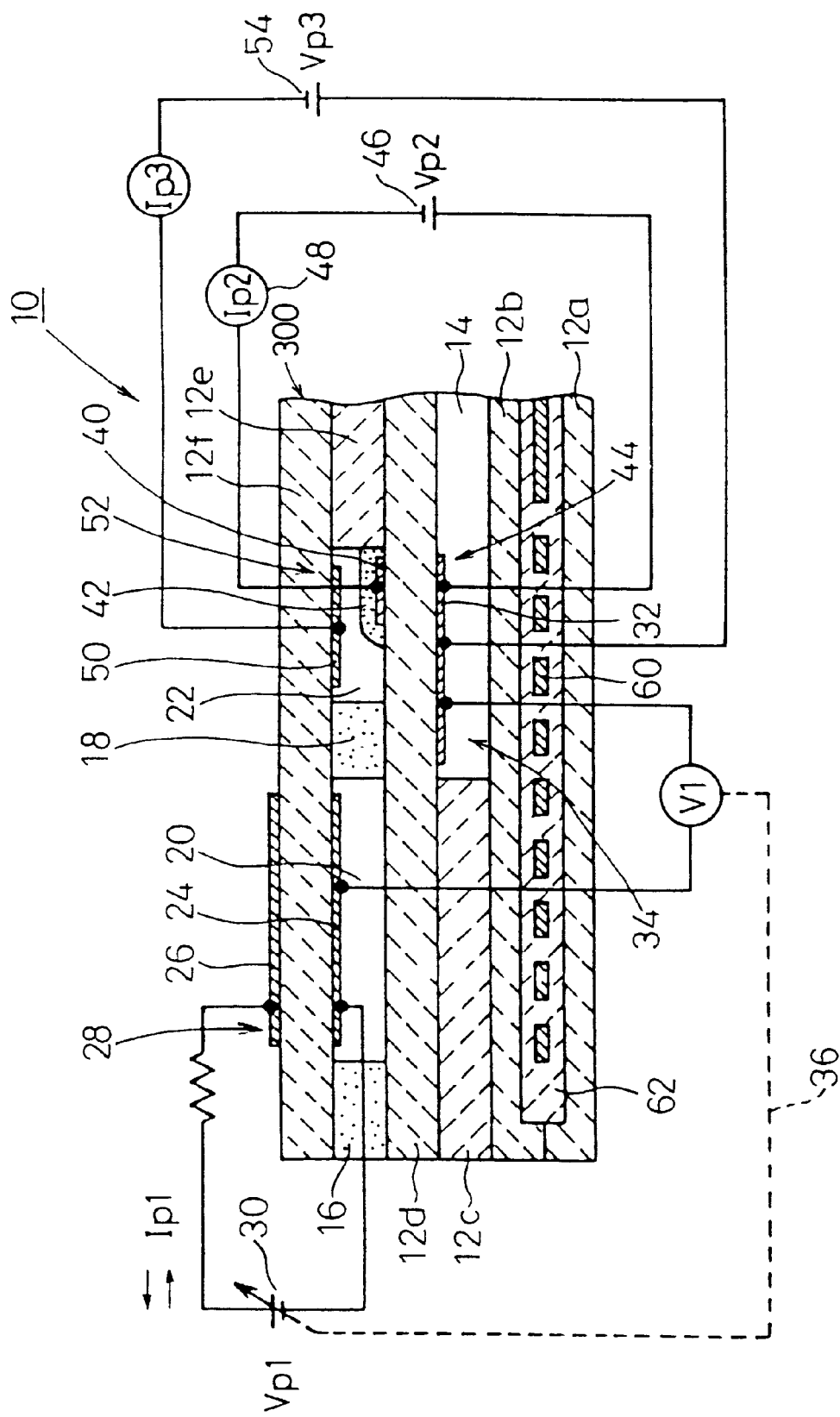
FIG. 1 shows an arrangement of a NOx sensor according to an embodiment of the present invention.

At first, as shown in FIG. 1, a NOx sensor 10 according to the embodiment of the present invention has a substrate 300 comprising, for example, six stacked solid electrolyte layers 12a to 12f composed of ceramics based on the use of oxygen ion-conductive solid electrolytes such as $ZrO_2$. The substrate 300 is constructed as follows. That is, first and second layers from the bottom are designated as first and second substrate layers 12a, 12b respectively. Third and fifth layers from the bottom are designated as first and second spacer layers 12c, 12e respectively. Fourth and sixth layers from the bottom are designated as first and second solid electrolyte layers 12d, 12f respectively.

Specifically, the first spacer layer 12c is stacked on the second substrate layer 12b. The first solid electrolyte layer 12d, the second spacer layer 12e, and the second solid electrolyte layer 12f are successively stacked on the first spacer layer 12c.

A space (reference gas-introducing space) 14, into which a reference gas such as atmospheric air to be used as a reference for measuring oxides is introduced, is formed between the second substrate layer 12b and the first solid electrolyte layer 12d, the space 14 being comparted by a lower surface of the first solid electrolyte layer 12d, an upper surface of the second substrate layer 12b, and side surfaces of the first spacer layer 12c.

The second spacer layer 12e is interposed between the first and second solid electrolyte layers 12d, 12f. First and second diffusion rate-determining sections 16, 18 are also interposed between the first and second solid electrolyte layers 12d, 12f.

A first chamber 20 for adjusting the partial pressure of oxygen in a measurement gas is formed and comparted by a lower surface of the second solid electrolyte layer 12f, side surfaces of the first and second diffusion rate-determining sections 16, 18, and an upper surface of the first solid electrolyte layer 12d. A second chamber 22 for finely adjusting the partial pressure of oxygen in the measurement gas and measuring oxides, for example, nitrogen oxides (NOx) in the measurement gas is formed and comparted by a lower surface of the second solid electrolyte layer 12f, a side surface of the second diffusion rate-determining section 18, a side surface of the second spacer layer 12e, and an upper surface of the first solid electrolyte layer 12d.

The external space communicates with the first chamber 20 via the first diffusion rate-determining section 16, and the first chamber 20 communicates with the second chamber 22 via the second diffusion rate-determining section 18.

The first and second diffusion rate-determining sections 16, 18 give predetermined diffusion resistances to the measurement gas to be introduced into the first and second chambers 20, 22 respectively. Each of the first and second diffusion rate-determining sections 16, 18 can be formed as a passage composed of, for example, a porous material, or a small hole having a predetermined cross-sectional area so that the measurement gas may be introduced.

Especially, a porous material composed of, for example, $ZrO_2$ is charged and arranged in the second diffusion rate-determining section 18. The diffusion resistance of the second diffusion rate-determining section 18 is made larger than the diffusion resistance of the first diffusion rate-determining section 16. The diffusion resistance of the second diffusion rate-determining section 18 is preferably larger than that of the first diffusion rate-determining section 16. However, no problem occurs even when the former is smaller than the latter.

The atmosphere in the first chamber 20 is introduced into the second chamber 22 under the predetermined diffusion resistance via the second diffusion rate-determining section 18.

An inner pumping electrode 24 having a substantially rectangular planar configuration and composed of a porous cermet electrode (for example, a cermet electrode composed of $Pt.ZrO_2$ containing 1% of Au) is formed on the entire lower surface portion for forming the first chamber 20, of the lower surface of the second solid electrolyte layer 12f. An outer pumping electrode 26 is formed on a portion corresponding to the inner pumping electrode 24, of the upper surface of the second solid electrolyte layer 12f. An electrochemical pumping cell, i.e., a main pumping cell 28 is constructed by the inner pumping electrode 24, the outer pumping electrode 26, and the second solid electrolyte layer 12f interposed between the both electrodes 24, 26.

A desired control voltage (pumping voltage) Vp1 is applied between the inner pumping electrode 24 and the outer pumping electrode 26 of the main pumping cell 28 by the aid of an external variable power source 30 to allow a pumping current Ip1 to flow in a positive or negative direction between the outer pumping electrode 26 and the inner pumping electrode 24. Thus, the oxygen in the atmosphere in the first chamber 20 can be pumped out to the external space, or the oxygen in the external space can be pumped into the first chamber 20.

A reference electrode 32 is formed on a lower surface portion exposed to the reference gas-introducing space 14, of the lower surface of the first solid electrolyte layer 12d. An electrochemical sensor cell, i.e., a controlling oxygen partial pressure-detecting cell 34 is constructed by the inner pumping electrode 24, the reference electrode 32, the second solid electrolyte layer 12f, the second spacer layer 12e, and the first solid electrolyte layer 12d.

The controlling oxygen partial pressure-detecting cell 34 is operated as follows. That is, an electromotive force is generated between the inner pumping electrode 24 and the reference electrode 32 on the basis of a difference in oxygen concentration between the atmosphere in the first chamber 20 and the reference gas (atmospheric air) in the reference gas-introducing space 14. The partial pressure of oxygen in the atmosphere in the first chamber 20 can be detected by using the electromotive force.

The detected value of the partial pressure of oxygen is used to feedback-control the variable power source 30. Specifically, the pumping action effected by the main pumping cell 28 is controlled by the aid of a feedback control system 36 so that the partial pressure of oxygen in the atmosphere in the first chamber 20 has a predetermined value which is sufficiently low to control the partial pressure of oxygen in the second chamber 22 in the next step.

The feedback control system 36 comprises a circuit to perform feedback control for the pumping voltage Vp1 between the outer pumping electrode 26 and the inner pumping electrode 24 so that the difference (detection voltage V1) between the electric potential of the inner pumping electrode 24 and the electric potential of the reference electrode 32 is at a predetermined voltage level. In this embodiment, the inner pumping electrode 24 is grounded.

Therefore, the main pumping cell 28 pumps out or pumps in oxygen in an amount corresponding to the level of the pumping voltage Vp1, of the measurement gas introduced into the first chamber 20. The oxygen concentration in the first chamber 20 is subjected to feedback control to give a predetermined level by repeating the series of operations described above. In this state, the pumping current Ip1, which flows between the outer pumping electrode 26 and the inner pumping electrode 24, represents the difference between the oxygen concentration in the measurement gas and the controlled oxygen concentration in the first chamber 20. The pumping current Ip1 can be used to measure the oxygen concentration in the measurement gas.

The porous cermet electrode, which constructs each of the inner pumping electrode 24 and the outer pumping electrode 26, is composed of a metal such as Pt and a ceramic such as $ZrO_2$. It is necessary to use a material which has a weak reducing ability or no reducing ability with respect to the NO component in the measurement gas, for the inner pumping electrode 24 disposed in the first chamber 20 to make contact with the measurement gas. It is preferable that the inner pumping electrode 24 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

In the NOx sensor 10 according to this embodiment, a detecting electrode 40 having a substantially rectangular planar configuration and composed of a porous cermet electrode is formed at a portion separated from the second diffusion rate-determining section 18, on an upper surface portion for forming the second chamber 22, of the upper surface of the first solid electrolyte layer 12d. An alumina film for constructing a third diffusion rate-determining section 42 is formed to cover the detecting electrode 40. An electrochemical pumping cell, i.e., a measuring pumping cell 44 is constructed by the detecting electrode 40, the reference electrode 32, and the first solid electrolyte layer 12d.

The detecting electrode 40 is composed of a porous cermet comprising zirconia as a ceramic and Rh as a metal capable of reducing NOx as the measurement gas component. Accordingly, the detecting electrode 40 functions as a NOx-reducing catalyst for reducing NOx existing in the atmosphere in the second chamber 22. Further, the oxygen in the atmosphere in the second chamber 22 can be pumped out to the reference gas-introducing space 14 by applying a constant voltage Vp2 between the detecting electrode 40 and the reference electrode 32 by the aid of a DC power source 46. The pumping current Ip2, which is allowed to flow in accordance with the pumping action performed by the measuring pumping cell 44, is detected by an ammeter 48.

The constant voltage (DC) power source 46 can apply a voltage of a magnitude to give a limiting current to the pumping for oxygen produced during decomposition in the measuring pumping cell 44 under the inflow of NOx restricted by the third diffusion rate-determining section 42.

On the other hand, an auxiliary pumping electrode 50 having a substantially rectangular planar configuration and composed of a porous cermet electrode (for example, a cermet electrode composed of Pt.ZrO$_2$ containing 1% of Au) is formed on the entire lower surface portion for forming the second chamber 22, of the lower surface of the second solid electrolyte layer 12f. An auxiliary electrochemical pumping cell, i.e., an auxiliary pumping cell 52 is constructed by the auxiliary pumping electrode 50, the second solid electrolyte layer 12f, the second spacer layer 12e, the first solid electrolyte layer 12d, and the reference electrode 32.

The auxiliary pumping electrode 50 is based on the use of a material having a weak reducing ability or no reducing ability with respect to the NO component contained in the measurement gas, in the same manner as the inner pumping electrode 24 of the main pumping cell 28. In this embodiment, it is preferable that the auxiliary pumping electrode 50 is composed of, for example, a compound having the perovskite structure such as La$_3$CuO$_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

A desired constant voltage Vp3 is applied between the reference electrode 32 and the auxiliary pumping electrode 50 of the auxiliary pumping cell 52 by the aid of an external power source 54. Thus, the oxygen in the atmosphere in the second chamber 22 can be pumped out to the reference gas-introducing space 14.

Accordingly, the partial pressure of oxygen in the atmosphere in the second chamber 22 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 28 for the first chamber 20, the change in amount of oxygen introduced into the second chamber 22 is greatly reduced as compared with the change in the measurement gas. Accordingly, the partial pressure of oxygen in the second chamber 22 is accurately controlled to be constant.

Therefore, in the NOx sensor 10 according to the embodiment of the present invention constructed as described above, the measurement gas, which has been controlled for the partial pressure of oxygen in the second chamber 22, is introduced into the detecting electrode 40.

As shown in FIG. 1, the NOx sensor 10 according to this embodiment further comprises a heater 60 for generating heat in accordance with electric power supply from the outside. The heater 60 is embedded in a form of being vertically interposed between the first and second substrate layers 12a, 12b. The heater 60 is provided in order to increase the conductivity of oxygen ion. An insulative layer 62 composed of alumina or the like is formed to cover upper and lower surfaces of the heater 60 so that the heater 60 is electrically insulated from the first and second substrate layers 12a, 12b.

The heater 60 is arranged over the entire portion ranging from the first chamber 20 to the second chamber 22. Accordingly, each of the first chamber 20 and the second chamber 22 is heated to a predetermined temperature. Simultaneously, each of the main pumping cell 28, the controlling oxygen partial pressure-detecting cell 34, and the measuring pumping cell 44 is also heated to a predetermined temperature and maintained at that temperature.

Next, the operation of the NOx sensor 10 according to the embodiment of the present invention will be explained. At first, the forward end of the NOx sensor 10 is disposed in the external space. Accordingly, the measurement gas is introduced into the first chamber 20 under the predetermined diffusion resistance via the first diffusion rate-determining section 16. The measurement gas, which has been introduced into the first chamber 20, is subjected to the pumping action for oxygen, caused by applying the predetermined pumping voltage Vp1 between the outer pumping electrode 26 and the inner pumping electrode 24 which construct the main pumping cell 28. The partial pressure of oxygen is controlled to have a predetermined value, for example, $10^{-7}$ atm. The control is performed by the aid of the feedback control system 36.

The first diffusion rate-determining section 16 serves to limit the amount of diffusion and inflow of oxygen in the measurement gas into the measuring space (first chamber 20) when the pumping voltage Vp1 is applied to the main pumping cell 28 so that the current flowing through the main pumping cell 28 is suppressed.

In the first chamber 20, a state of partial pressure of oxygen is established, in which NOx in the atmosphere is not reduced by the inner pumping electrode 24 in an environment of being heated by the external measurement gas and being heated by the heater 60. For example, a condition of partial pressure of oxygen is formed, in which the reaction of NO→½N$_2$+½O$_2$ does not occur, because of the following reason. That is, if NOx in the measurement gas (atmosphere) is reduced in the first chamber 20, it is impossible to accurately measure NOx in the second chamber 22 disposed at the downstream. In this context, it is necessary to establish a condition in the first chamber 20 in which NOx is not reduced by the component which participates in reduction of NOx (in this case, the metal component of the inner pumping electrode 24). Specifically, as described above, such a condition is achieved by using, for the inner pumping electrode 24, the material having a low ability to reduce NOx, for example, an alloy of Au and Pt.

The gas in the first chamber 20 is introduced into the second chamber 22 under the predetermined diffusion resistance via the second diffusion rate-determining section 18. The gas, which has been introduced into the second chamber 22, is subjected to the pumping action for oxygen, caused by applying the voltage Vp3 between the reference electrode 32 and the auxiliary pumping electrode 50 which constitute the auxiliary pumping cell 52 to make fine adjustment so that the partial pressure of oxygen has a constant and low value of partial pressure of oxygen.

The second diffusion rate-determining section 18 serves to limit the amount of diffusion and inflow of oxygen in the measurement gas into the measuring space (second chamber 22) when the voltage Vp3 is applied to the auxiliary pumping cell 52 so that the pumping current Ip3 flowing through the auxiliary pumping cell 52 is suppressed, in the same manner as performed by the first diffusion rate-determining section 16.

The measurement gas, which has been controlled for the partial pressure of oxygen in the second chamber 22 as described above, is introduced into the detecting electrode 40 under the predetermined diffusion resistance via the third diffusion rate-determining section 42.

When it is intended to control the partial pressure of oxygen in the atmosphere in the first chamber 20 to have a low value of the partial pressure of oxygen which does not substantially affect the measurement of NOx, by operating the main pumping cell 28, in other words, when the pumping voltage Vp1 of the variable power source 30 is adjusted by the aid of the feedback control system 36 so that the voltage V1 detected by the controlling oxygen partial pressure-detecting cell 34 is constant, if the oxygen concentration in the measurement gas greatly changes, for example, in a range of 0 to 20%, then the respective partial pressures of oxygen in the atmosphere in the second chamber 22 and in the atmosphere in the vicinity of the detecting electrode 40 slightly change in ordinary cases. This phenomenon is caused probably because of the following reason. That is, when the oxygen concentration in the measurement gas increases, the distribution of the oxygen concentration occurs in the widthwise direction and in the thickness direction in the first chamber 20. The distribution of the oxygen concentration changes depending on the oxygen concentration in the measurement gas.

However, in the case of the NOx sensor 10 according to this embodiment, the auxiliary pumping cell 52 is provided for the second chamber 22 so that the partial pressure of oxygen in its internal atmosphere always has a constant low value of the partial pressure of oxygen. Accordingly, even when the partial pressure of oxygen in the atmosphere introduced from the first chamber 20 into the second chamber 22 changes depending on the oxygen concentration in the measurement gas, the partial pressure of oxygen in the atmosphere in the second chamber 22 can be always made to have a constant low value, owing to the pumping action performed by the auxiliary pumping cell 52. As a result, the partial pressure of oxygen can be controlled to have a low value at which the measurement of NOx is not substantially affected.

NOx in the measurement gas introduced into the detecting electrode 40 is reduced or decomposed around the detecting electrode 40. Thus, for example, a reaction of NO→½N$_2$+½O$_2$ is allowed to occur. In this process, a predetermined voltage Vp2, for example, 430 mV (700° C.) is applied between the detecting electrode 40 and the reference electrode 32 which construct the measuring pumping cell 44, in a direction to pump out the oxygen from the second chamber 22 to the reference gas-introducing space 14.

Therefore, the pumping current Ip2 flowing through the measuring pumping cell 44 has a value which is proportional to a sum of the oxygen concentration in the atmosphere introduced into the second chamber 22, i.e., the oxygen concentration in the second chamber 22 and the oxygen concentration produced by reduction or decomposition of NOx by the aid of the detecting electrode 40.

In this embodiment, the oxygen concentration in the atmosphere in the second chamber 22 is controlled to be constant by means of the auxiliary pumping cell 52. Accordingly, the pumping current Ip2 flowing through the measuring pumping cell 44 is proportional to the NOx concentration. The NOx concentration corresponds to the amount of diffusion of NOx limited by the third diffusion rate-determining section 42. Therefore, even when the oxygen concentration in the measurement gas greatly changes, it is possible to accurately measure the NOx concentration, based on the use of the measuring pumping cell 44 by the aid of the ammeter 48.

According to the fact described above, almost all of the pumping current value Ip2 obtained by operating the measuring pumping cell 44 represents the amount brought about by the reduction or decomposition of NOx. Accordingly, the obtained result does not depend on the oxygen concentration in the measurement gas.

Next, a modified embodiment (10a) of the NOx sensor 10 according to the foregoing embodiment will be described with reference to FIG. 2. Components or parts corresponding to those shown in FIG. 1 are designated by the same reference numerals.

Figure 2:
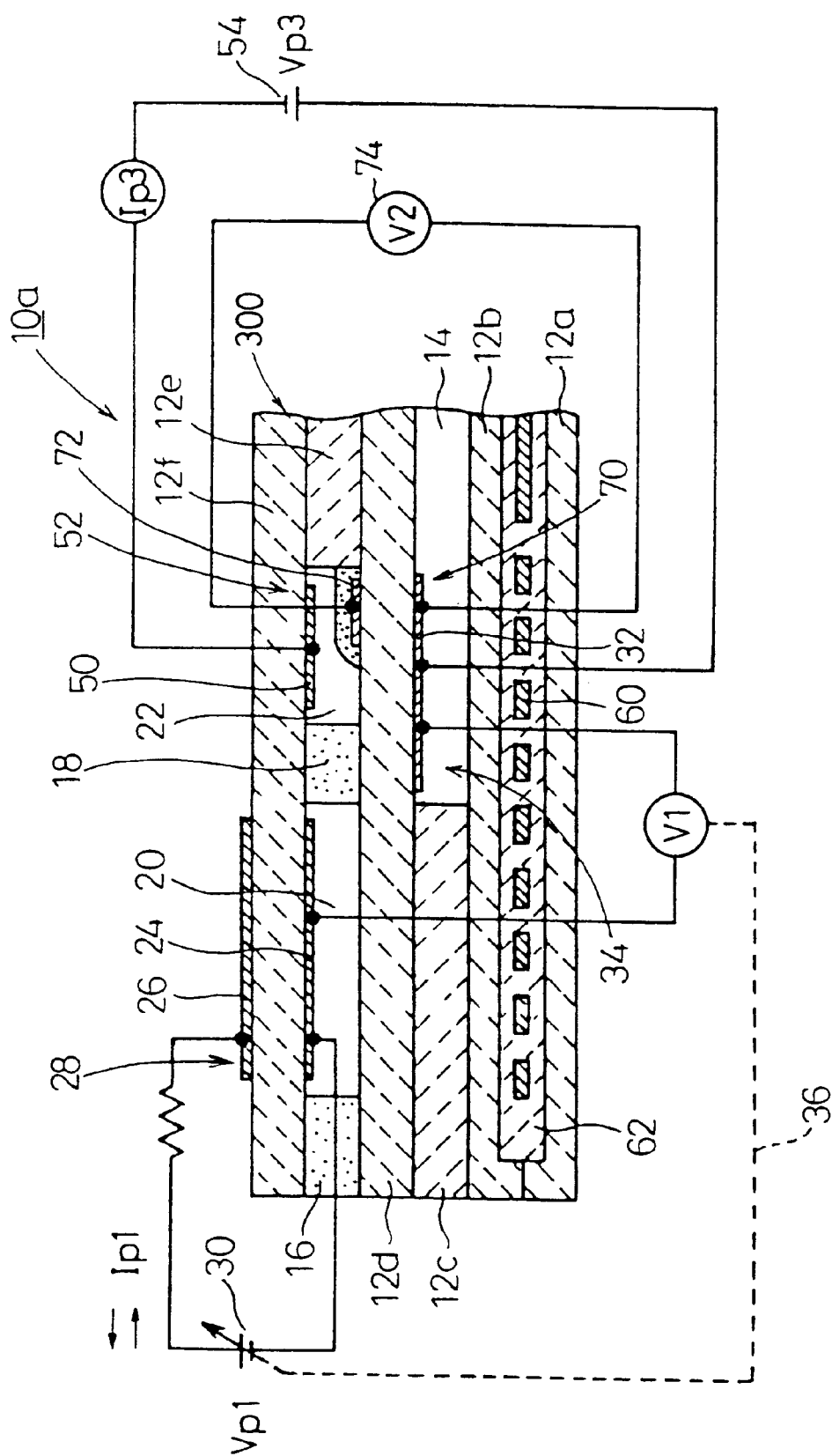
FIG. 2 shows an arrangement of a modified embodiment of the NOx sensor according to the embodiment of the present invention.

As shown in FIG. 2, a NOx sensor 10a according to the modified embodiment is constructed in approximately the same manner as the NOx sensor 10 according to the foregoing embodiment (see FIG. 1). However, the former is different from the latter in that a measuring oxygen partial pressure-detecting cell 70 is provided in place of the measuring pumping cell 44.

The measuring oxygen partial pressure-detecting cell 70 comprises a detecting electrode 72 formed on an upper surface portion for forming the second chamber 22, of the upper surface of the first solid electrolyte layer 12d, the reference electrode 32 formed on the lower surface of the first solid electrolyte layer 12d, and the first solid electrolyte layer 12d interposed between the both electrodes 72, 32.

In this embodiment, an electromotive force (electromotive force of an oxygen concentration cell) V2 corresponding to the difference in oxygen concentration between the atmosphere around the detecting electrode 72 and the atmosphere around the reference electrode 32 is generated between the reference electrode 32 and the detecting electrode 72 of the measuring oxygen partial pressure-detecting cell 70.

Therefore, the partial pressure of oxygen in the atmosphere around the detecting electrode 72, in other words, the partial pressure of oxygen defined by oxygen produced by reduction or decomposition of the measurement gas component (NOx) is detected as a voltage value by measuring the electromotive force (voltage V2) generated between the detecting electrode 72 and the reference electrode 32 by using a voltmeter 74.

Figure 3:
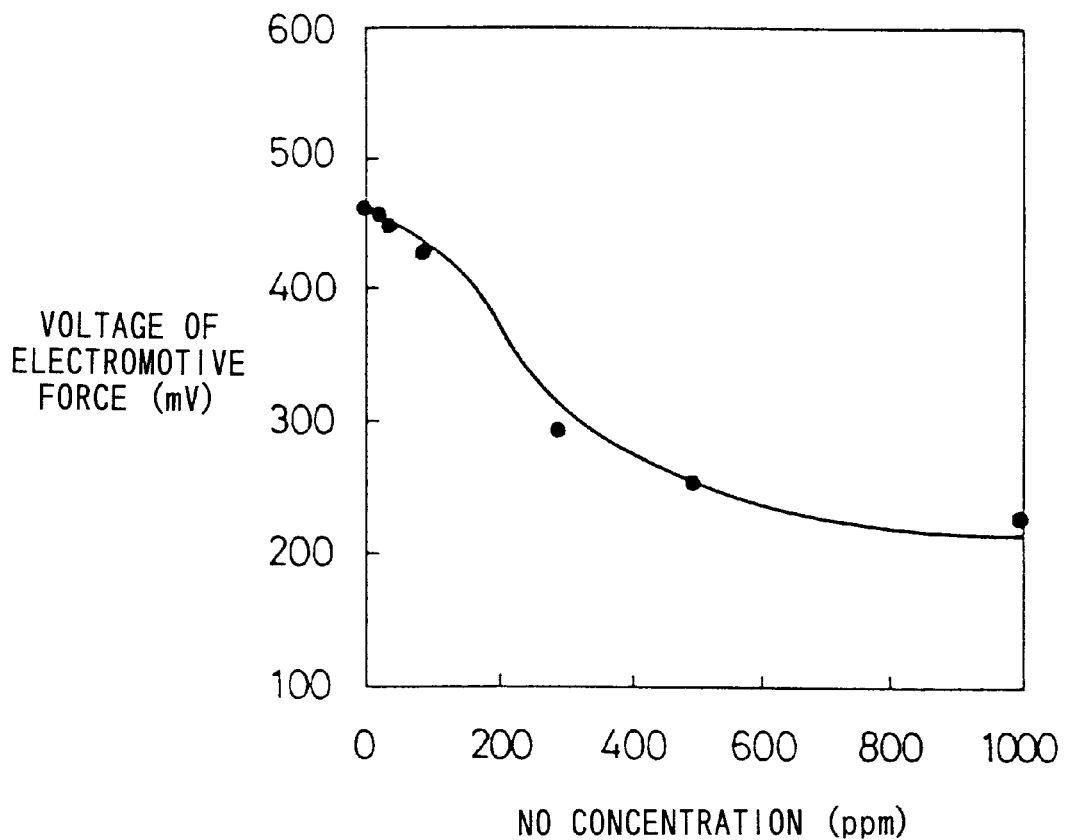
FIG. 3 shows a characteristic curve illustrating an output characteristic of the NOx sensor according to the modified embodiment.

The principle of detection performed by the NOx sensor 10a according to the modified embodiment will now be explained with reference to a characteristic curve shown in FIG. 3.

At first, when the NO concentration in the external space is 0 ppm, if the oxygen concentration in the atmosphere in the first chamber 20 is controlled by the aid of the feedback control system 36 so that the pumping voltage Vp1 for the main pumping cell 28 has a value ($10^{-7}$ atm) corresponding to 300 mV, then the oxygen concentration in the atmosphere in the second chamber 22 is also $10^{-7}$ atm. Further, when a predetermined voltage Vp3, for example, 460 mV (700° C.) is applied in a direction to pump out oxygen from the second chamber 22 to the reference gas-introducing space 14, between the auxiliary pumping electrode 50 and the reference electrode 32 which construct the auxiliary pumping electrode 52, the oxygen concentration in the second chamber 22 is $10^{-11}$ atm. Thus, the electromotive force (voltage V2), which is generated between the detecting electrode 72 and the reference electrode 32 of the measuring oxygen partial pressure-detecting cell 70, is about 460 mV.

When the NO concentration in the external space is gradually increased, then the reducing or decomposing reaction of NO is caused on the detecting electrode 72, and the oxygen concentration in the atmosphere around the detecting electrode 72 is increased, because the detecting electrode 72 also functions as a NOx-reducing catalyst in the same manner as the detecting electrode 40 of the measuring pumping cell 44 described above (see FIG. 1). Accordingly, the electromotive force, which is generated between the detecting electrode 72 and the reference electrode 32, is gradually decreased. With reference to FIG. 3 illustrating the characteristic curve, for example, when the NO concentration increases to 300 ppm, 500 ppm, and 1000 ppm, the electromotive force V2 detected by the voltmeter 74 is gradually decreased to 300 mV, 250 mV, and 220 mV respectively.

The degree of the decrease in electromotive force V2 represents the NO concentration. In other words, the electromotive force V2, which is outputted from the measuring oxygen partial pressure-detecting cell 70 constructed by the detecting electrode 72, the reference electrode 32, and the first solid electrolyte layer 12d, represents the NO concentration in the measurement gas.

Next, explanation will be made with reference to FIGS. 4 to 9 for a method for producing the NOx sensor 10 according to the foregoing embodiment (including the modified embodiment 10a), i.e., the production method according to the embodiment of the present invention.

Figure 4:
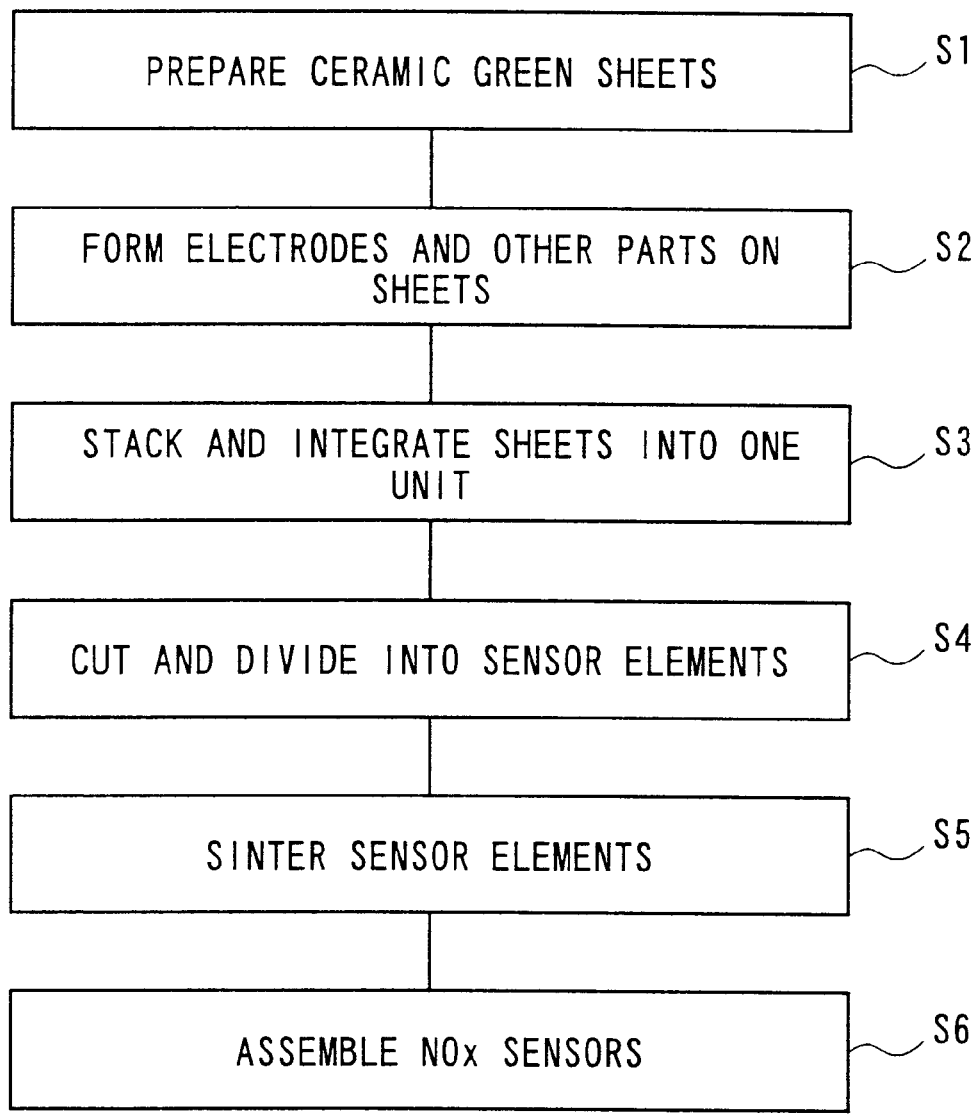
FIG. 4 shows a block diagram of steps illustrating a production method according to an embodiment of the present invention.

The production method according to this embodiment is carried out as shown in FIG. 4. At first, $ZrO_2$ powder, which is added with a stabilizer of $Y_2O_3$ in an amount of 4 molar %, is shaped into a form of tape to obtain ceramic green sheets (step S1). A pattern including, for example, electrodes, lead wires, and insulative layers, are formed on the obtained ceramic green sheets by means of, for example, screen printing (step S2). After completion of the pattern printing, the ceramic green sheets are stacked and integrated into one unit (step S3). Subsequently, the stacked compact is cut and divided into pieces each having a shape of a sensor element (step S4). After that, the respective sensor elements are sintered (step S5). The respective sensor elements are assembled into NOx sensors 10 (10a) (step S6).

The detecting electrode 40 or 72 is prepared with $Rh/ZrO_2=60/40\%$ by volume. In this embodiment, $ZrO_2$ was subjected to tentative sintering to have a lowered sintered property as compared with $ZrO_2$ used for the solid electrolyte substrate.

Figure 5:
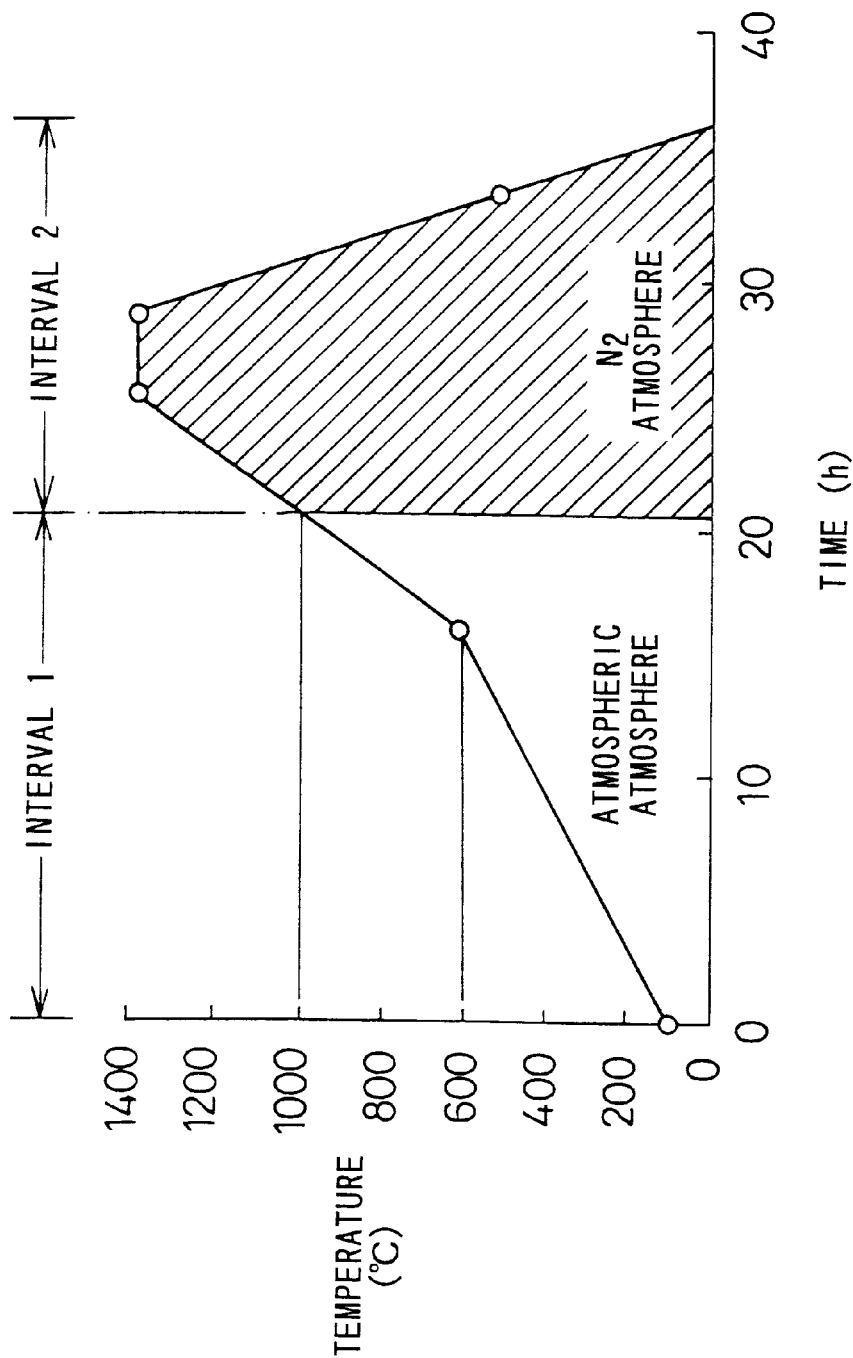
FIG. 5 shows a sequence illustrating a treatment process carried out in a sintering step.

The sintering step, which is represented by the step S5 in the production method according to this embodiment, is carried out, for example, in accordance with a sequence shown in FIG. 5. That is, the sintering is performed at a temperature-raising speed of 33° C./hour up to a point of time at which the temperature in the furnace arrives at about 600° C. from room temperature. The sintering is performed at a temperature-raising speed of 100° C./hour up to a point of time at which the temperature arrives at a maximum temperature of 1365° C. from the point of time at which the temperature is about 600° C. Subsequently, the maximum temperature is maintained for about 3 hours. After that, the temperature in the furnace is lowered in accordance with spontaneous radiational cooling. A binder or the like, which is contained, for example, in the ceramic green sheets, is removed at a temperature between about 600° C. and about 800° C. The binder is completely removed at a temperature between about 900° C. and about 1000° C.

In the sintering step described above, the sintering is performed in the atmospheric atmosphere in Interval 1 in which the temperature in the furnace is changed from room temperature to about 1000° C., while the sintering is performed in a nitrogen atmosphere in Interval 2 in which the temperature is changed from 1000° C. to the maximum temperature followed by the spontaneous radiational cooling.

That is, the atmosphere in the furnace is substituted with the nitrogen atmosphere to perform the sintering after the binder contained, for example, in the ceramic green sheets is completely removed. In the embodiment of the present invention, the sintering was performed by controlling the oxygen concentration in the atmosphere in the furnace to be 400 ppm in Interval 2. Nitrogen was injected during this process under the following condition. That is, nitrogen was injected at an injection speed of 10 (liters/minute) for about 10 minutes upon the substitution of the atmosphere in the furnace in which the temperature in the furnace was about 1000° C. Nitrogen was injected thereafter at an injection speed of 1 (liter/minute).

Explanation will now be made with reference to an illustrative experiment for the influence exerted on the detecting electrode 40 or 72 during the sintering process.

Figure 6:
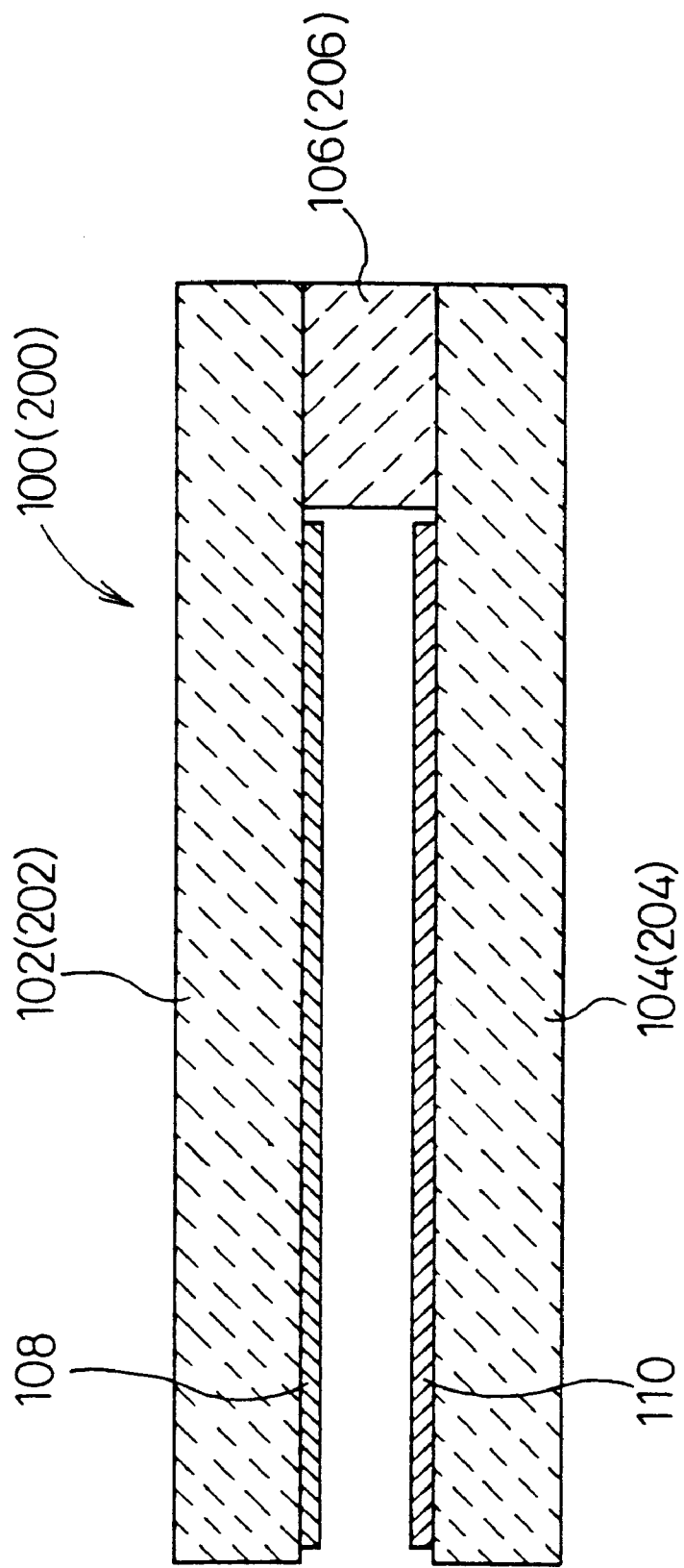
FIG. 6 shows a sectional view illustrating a sample and a stacked compact used for an experiment.

In this illustrative experiment, a sample 100 as shown in FIG. 6 was firstly produced. FIG. 6 is also used as a drawing to illustrate a laminated compact 200 of the ceramic green sheets as described later on, and the sample 100 after the sintering. In this experiment, a ceramic green sheet 202 disposed at the upper layer corresponds to an upper layer substrate 102, a ceramic green sheet 204 disposed at the lower layer corresponds to a lower layer substrate 104, and a ceramic green sheet 206 disposed at the intermediate layer corresponds to a connecting section 106.

The method for producing the sample 100 was carried out in approximately the same manner as the production method according to the embodiment of the present invention. That is, $ZrO_2$ powder, which is added with a stabilizer of $Y_2O_3$ in an amount of 4 molar %, is shaped into a form of tape to obtain three types of ceramic green sheets.

Of the three types of ceramic green sheets, a cermet electrode film 108 of Pt.ZrO$_2$ containing 1% Au was formed on a first principal surface of the ceramic green sheet 202 disposed at the upper layer. A cermet electrode film 110 of Rh.ZrO$_2$ was formed on a first principal surface of the ceramic green sheet 204 disposed at the lower layer. In this experiment, in order to easily conduct the component analysis based on the wet system, the area for forming the cermet electrode film 110 of Rh.ZrO$_2$ was fifty times the area for forming the equivalent film on the NOx sensor 10 (10a).

After that, the ceramic green sheet 206 disposed at the intermediate layer was used as the connecting section to stack and integrate the upper layer ceramic green sheet 202 and the lower layer ceramic green sheet 204 into one unit while their surfaces formed with the electrodes were opposed to one another. Thus, the laminated compact 200 as shown in FIG. 6 was produced. The laminated compact 200 was produced as a plurality of individuals.

The laminated compacts 200 were sintered under the following sintering conditions (atmospheres in the furnace) to produce the samples 100 as shown in FIG. 6. Five types of samples 100 were produced corresponding to the following five sintering conditions.

Sintering Condition 1: the atmospheric atmosphere was used from the start of the sintering to the end of the sintering;

Sintering Condition 2: the atmospheric atmosphere was used from room temperature to about 1000° C., and the oxygen concentration was controlled to be 1% from about 1000° C. to the end of the sintering;

Sintering Condition 3: the atmospheric atmosphere was used from room temperature to about 1000° C., and the oxygen concentration was controlled to be 0.25% from about 1000° C. to the end of the sintering;

Sintering Condition 4: the atmospheric atmosphere was used from room temperature to about 1000° C., and the oxygen concentration was controlled to be 100 ppm from about 1000° C. to the end of the sintering; and Sintering Condition 5: the atmospheric atmosphere was used from room temperature to about 1000° C., and the oxygen concentration was controlled to be 5 ppm from about 1000° C. to the end of the sintering.

Figure 7:
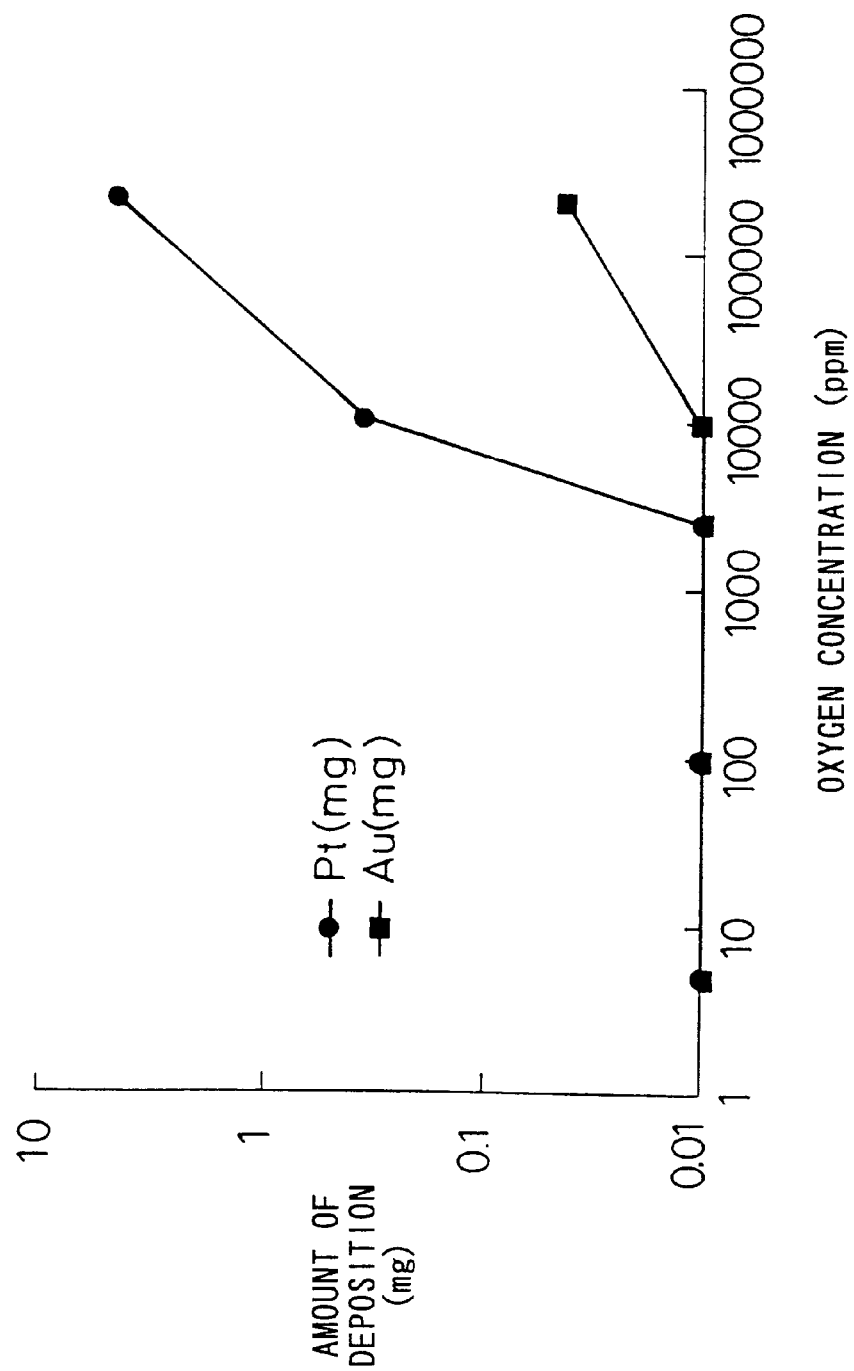
FIG. 7 shows the dependency on oxygen concentration, of the amount of deposition of Au/Pt on a cermet electrode film of $Rh.ZrO_2$.

Each of the five types of samples 100 produced under the five conditions described above respectively was divided (cut with a diamond cutter) at a position of the connecting section 106 to remove only the lower layer substrate 104. After that, the alloy, which was formed on the cermet electrode film 110 of Rh.ZrO$_2$ on the lower layer substrate 104, was dissolved in acid to elute the Pt component and the Au component. The amounts of deposition of the Pt component and the Au component were analyzed by means of the plasma spectrometric determination method. An obtained result is shown in FIG. 7. In FIG. 7, the result is plotted in the logarithmic scale on both of the vertical axis and the horizontal axis. According to the experimental result (FIG. 7), it is understood for Sintering Condition 1 that Pt is deposited in an amount of 5 mg, Au is deposited in an amount of 0.03 mg, and the volatilization due to oxidation of Pt is accelerated. As for Sintering Condition 2, no deposition of Au is observed, but Pt is deposited in an amount of 0.3 mg. According to this fact, it can be postulated that the formation of alloy of Rh, Pt, Au, and other components can be suppressed by controlling the oxygen concentration. This fact is verified by the sintering performed under Sintering Condition 3 and the followings described below.

That is, no deposition is observed at all for Pt and Au in Sintering Conditions 3 to 5. The formation of alloy on the cermet electrode film 110 of Rh.ZrO$_2$ is suppressed by controlling the oxygen concentration in the atmosphere in the furnace.

The boundary for the control of the oxygen concentration to obtain the NOx sensor 10 (10a) useful at the practical level is a line of oxygen concentration of 0.3%. On this condition, Pt is deposited in an amount of 0.05 mg. However, no problem occurs concerning the measurement accuracy in the case of application as the NOx sensor 10 (10a). The formation of alloy is not observed at a stage in which the oxygen concentration is controlled to be 0.25%. However, it is desirable that the oxygen concentration is preferably controlled to be not more than 500 ppm.

Explanation will now be made with reference to FIG. 8 for experimental results obtained to investigate the detection sensitivity to NO depending on the change in element temperature concerning an illustrative working sample and an illustrative comparative sample.

The illustrative working sample resides in a NOx sensor having approximately the same structure as that of the NOx sensor 10 according to the embodiment and produced by controlling the oxygen concentration to be about 400 ppm during the sintering process. The illustrative comparative sample resides in a NOx sensor having approximately the same structure as that of the NOx sensor 10 according to the embodiment and produced by executing the entire sintering process in the atmospheric atmosphere without controlling the oxygen concentration.

Figure 8:
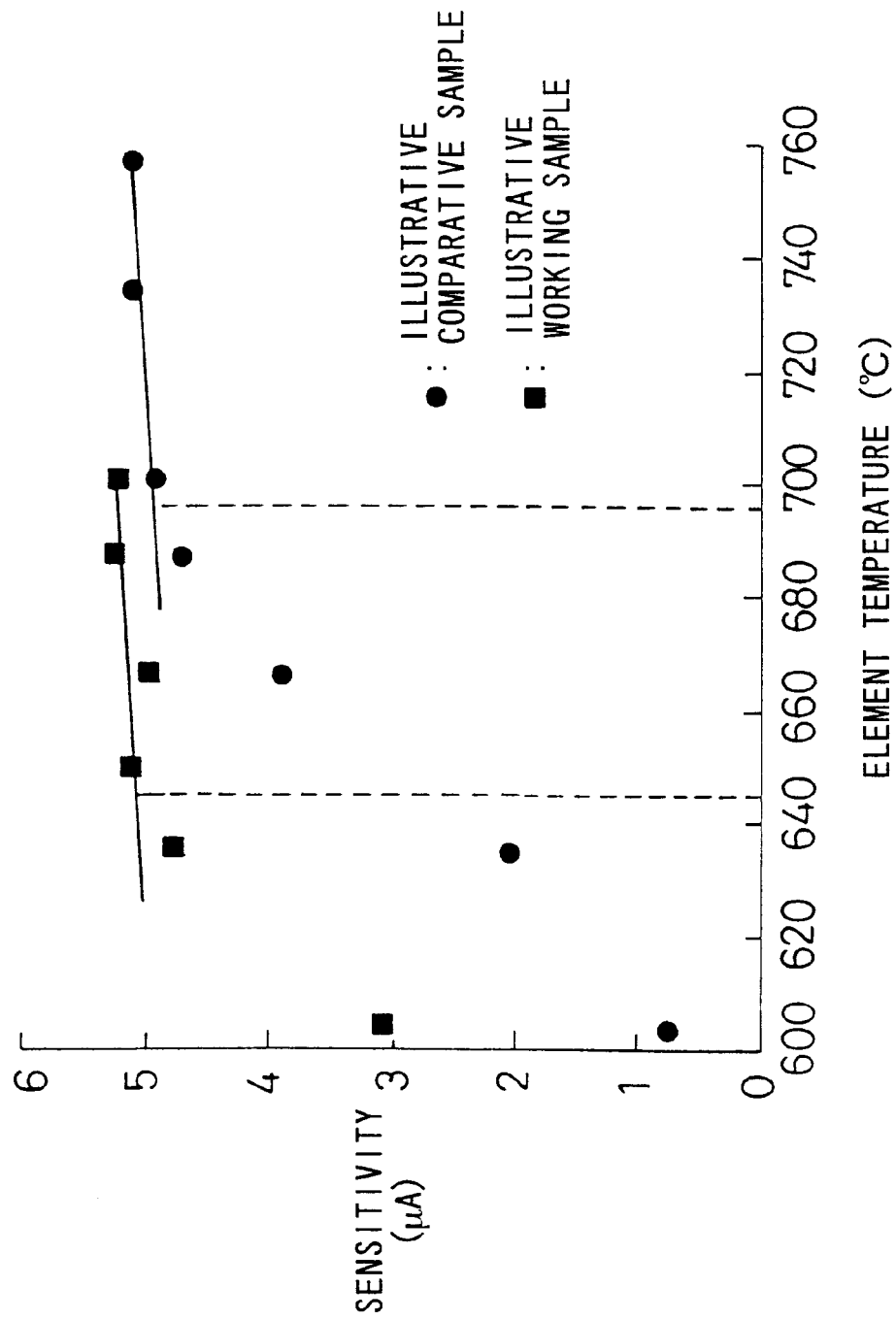
FIG. 8 shows characteristic curves illustrating the change in sensitivity at an NO concentration=1000 ppm depending on the change in element temperature.

Characteristic curves shown in FIG. 8 were obtained by plotting respective limiting current characteristics obtained by measuring, with the NOx sensors concerning the illustrative working sample and the illustrative comparative sample, a measurement gas provided by injecting nitrogen gas containing 1000 ppm of NO at 1 liter/minute respectively. The characteristic of the NOx sensor concerning the illustrative comparative sample is depicted by solid circles, and the characteristic of the NOx sensor concerning the illustrative working sample is depicted by solid squares.

The following features are appreciated from FIG. 8. That is, an approximately constant sensitivity is obtained in a certain temperature range for both of the illustrative working sample and the illustrative comparative sample. However, there is a certain temperature as a critical point, and the sensitivity is deteriorated when the element temperature is lower than the critical temperature.

The characteristic knee point, which represents the operation limit temperature, is about 695° C. for the illustrative comparative sample and about 645° C. for the illustrative working sample. The operation limit temperature for the illustrative working sample is lower than that for the illustrative comparative sample by about 50° C. It is understood that the low temperature operation performance is improved in the illustrative working sample.

Observed values of the detection output are as follows. That is, the output at an element temperature of about 645° C. is about 5 µA in the case of the illustrative working sample, and about 2 µA in the case of the illustrative comparative sample. It is understood that the detection output of the illustrative comparative sample is lower than that of the illustrative working sample by not less than ½.

Figure 9:
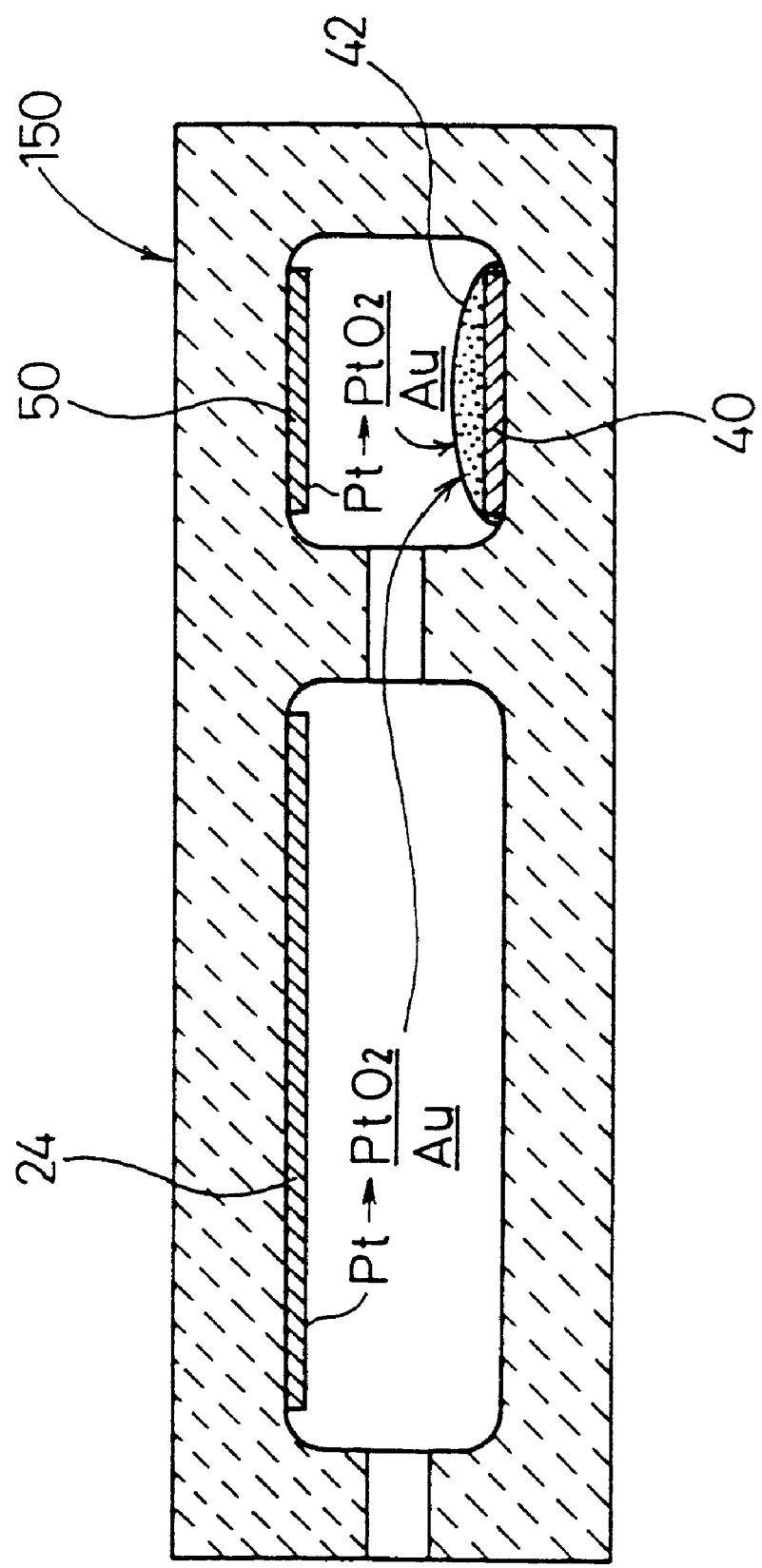
FIG. 9 illustrates the mechanism of alloy formation on a detecting electrode in a NOx sensor constructed for the purpose of comparison.

The result as described above is caused on the basis of the following reason as shown in FIG. 9. That is, in the NOx sensor 150 concerning the illustrative comparative sample, PtO$_2$, which is volatilized from the inner pumping electrode 24 and the auxiliary pumping electrode 50, is diffused up to the detecting electrode 40 to form the alloy together with Rh. Further, the volatilization of Pt is accelerated by the added Au. As a result, the catalytic activity is lowered on the detecting electrode 40 at a low temperature. FIG. 9 depicts only constitutive parts which relate to the alloy formation on the detecting electrode 40.

On the other hand, in the NOx sensor concerning the illustrative working sample, the oxygen concentration is controlled to be 400 ppm during the sintering step. Therefore, oxidation scarcely occurs on the inner pumping electrode 24 and the auxiliary pumping electrode 50. Accordingly, the diffusion of oxide to the detecting electrode 40 almost disappears. Thus, the alloy formation is suppressed on the detecting electrode 40.

As described above, the formation of alloy scarcely takes place on the detecting electrode 40, 72 in the NOx sensor 10 according to the embodiment of the present invention (including the modified embodiment 10a). Therefore, the low temperature operation performance is excellent, and it is possible to reliably improve the measurement accuracy.

In the production method according to the embodiment of the present invention, the sintering is performed in the atmospheric atmosphere in the sintering process in the step S5 shown in FIG. 4, especially in Interval 1 in which the temperature in the furnace is changed from room temperature to about 1000° C. The sintering is performed while controlling the oxygen concentration in the furnace in Interval 2 in which the temperature is raised from 1000° C. to the maximum temperature, and the temperature is lowered in accordance with the spontaneous radiational cooling. Therefore, oxidation scarcely occurs on the inner pumping electrode 24 and the auxiliary pumping electrode 50. Accordingly, the oxide is hardly diffused to the detecting electrode 40, 72, and thus the formation of alloy is suppressed on the detecting electrode 40, 72.

If the oxygen concentration in the sintering atmosphere is suppressed to be low in a state in which the binder remains in the substrate, the binder remains as carbon. Such carbon causes the following problem. That is, if the obtained element is used as a NOx sensor, the combustion of carbon occurs in accordance with the increase in element temperature, resulting in any error of the detection output.

However, in the production method according to the embodiment of the present invention, the atmosphere in the furnace is substituted with the nitrogen atmosphere after the binder contained in the ceramic green sheet or the like is completely removed to perform the sintering. Therefore, the output error does not occur, which would be otherwise caused by the residual of the binder as described above. Thus, it is possible to reliably improve the measurement accuracy of the NOx sensor 10 (10a).

In order to suppress the catalytic activity on the inner pumping electrode 24 and the auxiliary pumping electrode 50, Au, Ir, or various transition metals are added to the inner pumping electrode 24 and the auxiliary pumping electrode 50. However, the addition of such a component accelerates the volatilization of Pt which is the major component of the inner pumping electrode 24 and the auxiliary pumping electrode 50. On the contrary, in the present invention, the acceleration of volatilization of the major component is suppressed by controlling the oxygen concentration in the sintering atmosphere to be not more than 500 ppm. Accordingly, it is possible to effectively suppress the formation of alloy on the detecting electrode 40, 72.

In the embodiment described above, the atmosphere in the furnace is substituted from the atmospheric atmosphere to the nitrogen atmosphere at about 1000° C. However, the temperature at the point of time of the atmosphere substitution may be any degrees centigrade (° C.) provided that the temperature is not less than 400° C. at which the binder in the ceramic green sheet or the like is removed.

In the embodiment described above, the nitrogen atmosphere is used in Interval 2 ranging from about 1000° C. to the maximum temperature followed by the spontaneous radiational cooling. However, the atmosphere may be restored to the atmospheric atmosphere again during the temperature-lowering process after completion of the period in which the maximum temperature is maintained for the predetermined period of time. On such a condition, it is preferable that the introduction of the atmospheric atmosphere is started again at a temperature of not more than 1000° C.

In the embodiment described above, the oxygen concentration in the atmosphere in the furnace is controlled by changing the mixing ratio between the nitrogen gas and the atmospheric air. However, the oxygen concentration may be adjusted by mixing $H_2O$, $CO_2$, and nitrogen gas.

The control factor to achieve the effect of the present invention includes the oxygen concentration in the changed atmosphere, the maximum temperature during the sintering process, the temperature to start the atmosphere change, the temperature to end the atmosphere change, and the addition of the third component ($H_2$ and $CO_2$) to the changed atmosphere. The control factor may be appropriately adjusted depending on the solid electrolyte material and the electrode material to be used.

It is a matter of course that the method for producing the electrochemical element and the electrochemical element according to the present invention are not limited to the embodiments described above, which may be embodied in other various formed without deviating from the gist or essential characteristics of the present invention.

As explained above, according to the method for producing the electrochemical element and the electrochemical element, it is possible to suppress the alloy formation, for example, on the detecting electrode for detecting the measurement gas component (for example NOx), and it is possible to improve the measurement accuracy of the electrochemical element.

What is claimed is:

1. A method for producing an electrochemical element based on a limiting current system comprising at least a Pt-containing electrode and a Rh-containing electrode arranged in one internal space which is provided in a substrate of a $ZrO_2$ solid electrolyte or in a plurality of internal spaces which communicate with each other, said method comprising the steps of:

forming said electrodes on ceramic green sheets; and
   stacking and integrating said ceramic green sheets into one unit followed by sintering to prepare said substrate wherein:
   an oxygen concentration is controlled to be greater than 0% and not more than 0.5% in a sintering atmosphere after removal of a binder in said step of sintering said substrate.

2. The method for producing said electrochemical element according to claim 1, wherein said oxygen concentration in said sintering atmosphere is controlled to be not more than 500 ppm.

3. The method for producing said electrochemical element according to claim 1, wherein said sintering step is started from an atmospheric atmosphere, and said control of said oxygen concentration is started from a predetermined temperature.

4. The method for producing said electrochemical element according to claim 3, wherein said control of said oxygen concentration is started at a temperature of not less than 400° C.

5. The method for producing said electrochemical element according to claim 1, wherein a state of controlling said oxygen concentration is restored again to an atmospheric atmosphere during a process of lowering the temperature after completion of maintenance of a maximum temperature for a predetermined period of time during said sintering step.

6. The method for producing said electrochemical element according to claim 5, wherein introduction of said atmospheric atmosphere is started again at a temperature of not more than 1000° C.

7. The method for producing said electrochemical element according to claim 1, wherein $H_2O$ or $CO_2$ is added to an atmosphere in which said oxygen concentration is controlled in said sintering atmosphere.

8. An electrochemical element comprising:
  one internal space which is provided in a substrate of a $ZrO_2$ solid electrolyte, or a plurality of internal spaces which communicate with each other; and
  at least one Pt-containing electrode and a Rh-containing electrode arranged in said internal space or in said internal spaces, wherein:
  at least said substrate is formed by heating to remove a binder therefrom and then sintering an integrated unit of stacked ceramic green sheets carrying said electrodes, in an atmosphere in which oxygen concentration is controlled to be greater than 0% and not more than 0.5% in a predetermined temperature region.

* * * * *